United States Patent
Zarrinpashne et al.

(10) Patent No.: US 7,902,113 B2
(45) Date of Patent: Mar. 8, 2011

(54) CATALYST DIRECT CONVERSION OF METHANE TO ETHANE AND ETHYLENE

(75) Inventors: Saeed Zarrinpashne, Tehran (IR); Reza Ahmadi, Tehran (IR); Seyyed Madjid Zekordi, Tehran (IR)

(73) Assignee: Research Institute of Petroleum Industry (RIPI), Tehran (IR)

( * ) Notice: Subject to any disclaimer, the term of this patent is extended or adjusted under 35 U.S.C. 154(b) by 772 days.

(21) Appl. No.: 11/220,740

(22) Filed: Sep. 6, 2005

(65) Prior Publication Data

US 2006/0155157 A1 Jul. 13, 2006

(30) Foreign Application Priority Data

Sep. 6, 2004 (EP) .................................... 04104290

(51) Int. Cl.
  *B01J 23/04* (2006.01)
  *B01J 23/20* (2006.01)
  *B01J 23/34* (2006.01)
  *B01J 23/888* (2006.01)
  *C07C 4/06* (2006.01)

(52) U.S. Cl. ......... 502/300; 502/317; 502/324; 502/330; 502/353; 502/311; 502/305; 502/302; 502/344; 585/650; 585/651; 585/943

(58) Field of Classification Search .................. 502/311, 502/240, 243, 246, 254, 300, 302, 305, 317, 502/324, 330, 344, 353; 585/943, 650, 651
See application file for complete search history.

(56) References Cited

U.S. PATENT DOCUMENTS

| | | | |
|---|---|---|---|
| 4,523,050 A | 6/1985 | Jones et al. | |
| 4,554,395 A | 11/1985 | Jones et al. | |
| 4,560,821 A | 12/1985 | Jones et al. | |
| 4,695,668 A * | 9/1987 | Velenyi | 585/500 |
| 4,777,313 A | 10/1988 | Sofranko et al. | |
| 4,939,310 A | 7/1990 | Wade | |
| 4,968,661 A * | 11/1990 | Teller et al. | 502/304 |
| 5,105,053 A * | 4/1992 | Jacobson et al. | 585/658 |
| 5,817,904 A | 10/1998 | Vic et al. | |
| 6,403,523 B1 | 6/2002 | Cantrell | |
| 6,518,476 B1 | 2/2003 | Culp | |
| 6,596,912 B1 | 7/2003 | Lunsford | |
| 2002/0173410 A1 | 11/2002 | Liao | |

FOREIGN PATENT DOCUMENTS

WO 02/22258 3/2002

OTHER PUBLICATIONS

A.G. Dedov. A.S. Loktev, I.I. Moiseev, A. Aboukais, J.-F. Lamonier, I.N. Filimonov, "Oxidative coupling of methane catalyzed by rare earth oxides Unexpected synergistic effect of the oxide mixtures," Applied Catalysis A: General 245 (2003), pp. 209-220.*
Alejandra Palermo, Juan Pedro Holgado Vazquez, Adam F. Lee, Mintcho S. Tikhov, and Richard M. Lambertz, "Critical Influence of the Amorphous Silica-to-Cristobalite Phase Transition on the Performance of Mn/Na2WO4/SiO2 Catalysts for the Oxidative Coupling of Methane," Journal of Catalysis 177, (1998), pp. 259-266.*
Masami Yamamura, Hideo Okado, and Naohide Tsuzuki, "Group 5A Metal Oxides as Promoters for Oxidative Coupling of Methane" Chemistry Letters The Chemical Society of Japan (1992), pp. 203-206.*
Ji et al. "The Relationship Between the Structure and the Performance of Na-W-Mn/SiO2 Catalysts for the -Oxidative Coupling of Methane." Applied Catalysis A: General 225, 2002, pp. 217-284.
Ji et al. "Surface W04 Tetrahedron: the Essence of the Oxidative Coupling of Methane over M-W-Mn/SiO2 Catalysts." Journal of Catalysts 220, 2003, pp. 47-56.

* cited by examiner

*Primary Examiner* — Timothy C Vanoy
*Assistant Examiner* — Diana J Liao
(74) *Attorney, Agent, or Firm* — Kenyon & Kenyon LLP

(57) ABSTRACT

The present invention relates to an improved catalyst for direct conversion of methane to ethane and ethylene, a method for producing the catalyst and a process making use of the catalyst.

15 Claims, No Drawings

US 7,902,113 B2

CATALYST DIRECT CONVERSION OF METHANE TO ETHANE AND ETHYLENE

This application claims the benefit under 35 U.S.C. § 1.119 (a) of European Patent Application No. 04104290.4, filed Sep. 6, 2004, the contents of which is incorporated herein by reference.

FIELD OF THE INVENTION

The present invention relates to an improved catalyst for direct conversion of methane to ethane and ethylene, a method for producing the catalyst and a process making use of the catalyst.

BACKGROUND OF THE INVENTION

Natural gas, which is the major source of methane, is usually used as a fuel. The amount of methane present in natural gas varies between 40 to 95 volume percents, depending on its source.

Large scale transportation and utilization of natural gas, however, requires sophisticated pipeline systems which are expensive as such and still further their maintenance is time consuming and costly.

Liquefaction of natural gas is proposed as an alternative method for natural gas transportation, but liquefaction, transfer and re-vaporization of the produced liquid is not only complex and energy consuming, but it also requires very expensive safety systems. Therefore, if methane present in the natural gas can be converted to more easily transportable and more valuable products, such as ethylene and ethane, natural gas utilization will become more efficient and more economical.

At present, the naphta cut produced from fractional distillation of crude oil is the major source of ethylene. Due to increased demand for gasoline, supplying naphta to petrochemical complexes is becoming more and more difficult every day. As a result, the usage of natural gas as a new source of ethylene becomes important.

Since 1982, when Keller and Bhasin first introduced the direct conversion of methane to ethylene, a lot of research work has been carried out in this field. The major problem toward commercialization of this process has been its low yield during the ethane and ethylene production. Reasons for that are undesired methane combustion reactions, which in turn convert some of the methane to carbon monoxide and carbon dioxide. Many efforts for improving the process focused on production of catalysts, which can increase the yields of ethane and ethylene.

According to the prior art, studies, for example a study by Lunsford, compare three types of catalysts useful during a process for producing ethylene: (a) catalysts including manganese and tungsten oxides supported on silicon oxide (silica), (b) catalysts based on barium oxide supported on magnesium oxide and (c) catalysts based on strontium oxide supported on lanthanum oxide.

The catalyst comprising manganese and tungsten oxides supported on silica has shown methane conversion rates of up to 37% and C2-hydrocarbon selectivity of up to 65% at feed flow rates of 1320 ml/min per gram of the catalyst. The initial feed gas comprised 45% methane, 15% oxygen, and 30% an inert gas (by volume), and the process was run under atmospheric pressure.

In 1995, Ding-Jum and co-workers studied two types of catalysts: a manganese tungsten based catalyst supported on silica and also manganese tungsten based catalyst supported on magnesium oxide. A maximum performance was observed for the manganese tungsten based catalyst supported on silica. Such maximum conversion rates correspond to a methane conversion of about 20%, and a C2-hydrocarbon selectivity of about 80%. This performance was achieved at temperatures of 800° C., a methane to oxygen ratio of 7.3 and feed flow rate of 383 ml/min per gram catalyst.

A quite recently published prior art study dated 2002 (author: Sheng-Fu-Ji) reports on a manganese tungsten based catalyst supported on silica. It was found that a maximum C2-hydrocarbon yield amounts to about 19.2% (corresponding to methane conversion of 32.7%) with a C2-hydrocarbon selectivity of 58.6% at a temperature of 800° C., a methane to oxygen ratio of 3 and a feed flow rate of 600 ml/min per gram catalyst, carried out under atmospheric pressure.

In 2003 Shuben Li issued a review paper on the performance of manganese oxide based catalysts supported on silica, promoted by various elements. It was suggested to add a second active component (as sodium tungstate) to a manganese based catalyst supported on silica. As such component a transition metal oxide was used and led to an improvement of the catalytic behaviour. It is reported about a C2 hydrocarbon yield of 23.9% and a selectivity of 64.9% for C2-hydrocarbons at a temperature of 800° C. under atmospheric pressure with a feed flow rate of about 600 ml/min per gram catalyst and a methane to oxygen ratio of 3, provided that 40 vol. % of inert gas are present in the feed gas.

One should bear in mind that the processes described in the aforementioned prior art suffer from the drawback of a rather low C2-hydrocarbon selectivity, which results in the inability for the respective process to be commercialized under economically feasible conditions.

U.S. Pat. No. 4,560,821, U.S. Pat. No. 4,523,050 and U.S. Pat. No. 4,554,395 refer to a group of catalysts wherein the major components are reducible oxides selected from the group of Mn, Sn, In, Ge, Pb, Sb, and Bi.

U.S. Pat. No. 4,777,313 discloses a catalyst family with superior performance compared to the performance described in the before mentioned patent documents. In addition to reducible metal oxides the catalysts described also contains Boron (B) and one element selected from alkali metals or alkaline earth metals as promoter.

In U.S. Pat. No. 5,817,904 yet another group of catalysts are described, which are based on manganese oxide supported on silica and promoted by one alkali metal and one non-metal with a definite molar ratio of non-metal to alkaline metal.

U.S. Pat. No. 4,939,310 refers to catalysts containing manganese oxide in combination with an element from the group of Sn, Ti, W, Ta, Si, Ge, Pb, P, As, Sb, B, Ga or an element from the Lanthanide or Actinide families, which catalysts are promoted with halogen salts of one of alkali or alkaline earth metals.

The catalysts containing halogen elements, however, are subject to the drawback of gradual deactivation due to gradual loss of halogen elements, which in turn leads to an unstable performance at long term operation. As a consequence, the processes cannot be subject to industrial application under an economic point of view.

Hence, there is a strong need to provide a catalyst useful in a process for producing C2-hydrocarbons, such as ethane and ethylene, by direct conversion of methane which catalyst and process show superior quality and efficiency under long term conditions with still a high selectivity of C2-hydrocarbons.

SUMMARY OF THE INVENTION

It has now been surprisingly found that catalysts based on a reducible metal oxide selected from oxides of Mn, Sn, In, Ge, Pb, Sb, Bi, Pr, Tb, Ce, Fe, and Ru, supported on silica and promoted by addition of tungsten and an alkali metal, which catalyst still further comprises niobium as promoter and optionally a metal selected from Eu, Y and Nd, show an excellent long term stability and lead to high conversion rates during an OCM (oxidative coupling of methane) process while simultaneously the selectivity toward C2-hydrocarbons is high. In a preferred embodiment, the promoter to be used is niobium oxide. The alkali metal to be used within the catalyst can, for example, be sodium.

According to the OCM process claimed in this invention, the method for producing ethane and ethylene during an OCM process leads to higher yields. The gas used for feeding comprises a mixture of methane and oxygen and an inert gas, as for example nitrogen, helium or argon. The feed gas passes over the catalyst and the resulting yield of C2 hydrocarbons is superior at a temperature of from 600 to 950° C., preferably at a temperature of from 700 to 850° C.

As described before, the catalyst comprises a reducible metal oxide, as for example, manganese oxide, silicon oxide (as base), an alkali metal, as for example sodium, tungsten and still further niobium, as promotor. A further metal optionally present in the catalyst is selected from the group consisting of Eu, Y and Nd. One or more of the compounds are present as oxides in amount sufficient to substantially increase the C2 hydrocarbon yield of the process when compared with the yield that can be achieved with a catalyst comprising no niobium as promoter.

The reducible metal oxide is selected from oxides of Mn, Sn, In, Ge, Pb, Sb, Bi, Pr, Tb, Ce, Fe, and Ru.

According to a preferred embodiment, niobium is present in the catalyst in an amount of from 0.5 to 5% by weight based on the total amount of the catalyst preferably in an amount of from 1.2 to 4% by weight and in a most preferred embodiment in an amount of 1.9% by weight. In a most preferred embodiment the promoter is niobium oxide.

In a preferred catalyst the atomic ratio of reducible metal to tungsten is in the range of from 1.8 to 3.5 In a preferred catalyst the atomic ratio of the reducible metal oxide to alkaline metal is in the range of from 0.1 to 0.60.

In a preferred catalyst the atomic ratio of the promotor to reducible metal is in the range of from 0.01 to 0.8. In a preferred catalyst the atomic ratio of the reducible metal to the silica is in the range of from 0.005 to 0.03.

In accordance with the invention, the solid catalyst can, for example, be used in an immobilized form, such as in the form of a fixed bed reactor.

During contact of methane with the catalyst and the subsequent reduction of metal oxides, particularly manganese oxide, methane is converted to ethane while water is formed as a by-product. Oxygen present in the feed gas simultaneously oxidizes the reduced metal oxide, as for example manganese to manganese oxide, again, i.e. leads to a recovery of the catalyst and keeps the process stable.

Carbon monoxide and carbon dioxide are produced in minor amounts only as a result of undesired combustion reactions. As a result of thermal cracking of produced ethane, also hydrogen and ethylene will be produced.

By adjusting the operating conditions, including methane to oxygen ratio in the feed gas, the residence time of the gas mixture passing over the catalyst bed, temperature and pressure, the ethane and ethylene production yield can be increased up to 28%, that is a methane conversion level of about 35% and an ethane and ethylene selectivity of about 80% (see the example 2).

For example, the methane to oxygen ratio in the inlet feed is in the range of from 2 to 20 and more preferably in the range of from 3 to 10.

A suitable percentage of inert gas in the feed stream is in the range of from 0 to 80 vol. %, preferably 50-70 vol. %. The inert gas can be, for example, nitrogen, helium, or argon.

A suitable ratio of the volumetric flow of the gas feed to the solid bulk volume is in the range of from 10,000 to 60,000 per hour.

As to the pressure of gas inside the reactor, values of from 0 to 3 atm. are possible.

According to a most preferred embodiment of the present invention, the catalyst comprises
1.9% Nb
2% Mn
1.8% Na
2.8% W
rest $SiO_2$.

Also encompassed by the present invention is a method for producing the catalyst.

In general, the reducible metal in the catalyst is provided as soluble salt. For manganese, such as suitable salt is manganese nitrate. For providing the tungsten and sodium elements to the catalyst, for example a sodium tungstate ($Na_2 WO_4$) solution is used.

For providing niobium or any other metal to the catalyst, a suitable soluble salt can be used. During the catalyst synthesis and after its calcinations, the metal compound will change to its oxide. For example, manganese will be present in the final catalyst as manganese oxide, tungsten and sodium will be present in the form of conjugate tungsten-sodium oxide (with the formula of $Na_4 WO_4$) and niobium will be present in the form of the respective oxide, namely niobium oxide.

Useful are methods of co-precipitation and impregnation. In the co precipitation method, a soluble manganese salt, such as manganese nitrate, and sodium tungstate solutions are used. The silica or silicon oxide as the support of the active catalyst sites is made by mixing sodium silicate with sulfuric acid. After the addition of stoichiometric amounts (as required) of these solutions, a precipitate is formed. The precipitate is then filtered off from the mixture, and is dried in an oven (130° C.), and is then calcinated in a furnace for 10 to 15 hours at temperatures of from 800 to 1100° C. The particles are then processed into pellets, crushed and sieved to obtain particles with a size range of from 40 to 120 microns. In a next step, these particles are added to a solution of a niobium compound, such as niobium chloride($NbCl_5$), and the process of filtration, drying and calcination is repeated. The resulting calcinated particles are again processed into pellets, crushed and sieved, using 20-35 mesh sieves. The resulting particles can be used during the methane conversion process.

According to an alternative route, the catalyst support (silica) is prepared first via precipitation, resulting from mixing of sodium silicate solution and sulfuric acid solution.

This product is filtered off from the primary slurry, dried in an oven (130° C.) and calcinated at 800 to 1300° C. in a furnace. After the calcination stage, solutions of manganese salt such as manganese nitrate and sodium tungstate are successively impregnated to the support. The resulting solid is filtered again, dried in an oven and calcinated at 800 to 1100° C. Then the desired amount of the niobium compound is impregnated on the calcinated solid via one of its soluble salts, such as for example niobium chloride ($NbCl_5$) Finally, the filtering, drying and calcination processes are repeated as described for the previous stages. The final particles are processed into pellets, crushed, and particles having a mesh size of from 25-35 were separated using a sieve, and prepared for the methane conversion process.

During the process of converting methane to C2 hydrocarbons, for example 0.5 to 2.0 gram of the catalyst are loaded into a quartz tube having an outer diameter of 12 mm. This tube is placed in an electrical furnace. The temperature of the catalyst bed (the zone containing the catalyst particles) is measured using a thermocouple placed at the middle of catalyst bed and connected to a temperature controller. A preferred range of the reactor temperature is in the range of from 600 to 950° C., preferably an accuracy of 1° C. is to be achieved.

The feed stream is prepared by mixing separate streams of methane, oxygen and an inert gas, such as, for example, nitrogen, helium or argon. The flow rates of each constituent are accurately adjusted and controlled using precision electronic mass flow controllers to the values depicted by the amount of charged catalyst and the required methane to oxygen ratio, which can be for example in the range of from 2 to at least 20, and preferably in the range of from 3 to 10, as well as the inert gas volume percentage in the feed. To obtain a homogeneous feed gas, all of the initial gas streams are directed to a static mixer. The effluent stream from the static mixer is fed to the reactor inlet. In the catalyst bed, the coupling reaction of methane to ethane also dehydrogenation of ethane to ethylene and undesired combustion reactions resulting in carbon monoxide and carbon dioxide as by-products take place. Hence, the effluent stream from the reactor contains besides unreacted methane and oxygen, the end product ethane but still further ethylene, water, carbon monoxide, carbon dioxide and hydrogen. This stream is cooled down in a condenser in order to separate its water as a liquid stream. A part of the remaining gas is sent to a gas chromatograph after the condensating step for determination of the products formed during the reaction.

By measuring the volumetric flow rate of feed and product gases, calculations as to performance of the reaction in terms of methane conversation are made, taking into consideration the initial feed and final product gas composition. The methane conversion rate in percent is the percentage of methane that enters to the reactions. The C2 hydrocarbon selectivity is expressed in percent of methane converted to C2 hydrocarbons relative to the total converted methane, and the C2 hydrocarbon yield is the percentage of methane converted to C2 hydrocarbons relative to total amount of methane that was fed to the reactor.

DETAILED DESCRIPTION OF PREFERRED EMBODIMENTS

Example 1

Following the general methods described above, two sample catalysts, one in accordance with the invention and another as comparative catalyst, have been produced with the following stoichiometric formulas (figures are in weight percent):

comparative catalyst A): 2.1% Mn, 1.2% Na, 2.7% W and rest $SiO_2$ catalyst according to the invention B): 1.8% Mn, 1.8% Na, 2.8% W, 1.9% Nb and rest $SiO_2$ The following two examples show the results of performance evaluations based on the use of the two catalysts in a system as described in the introductory part above. "S" denotes selectivity, "X" denotes conversion and "Y" denotes yield.

Comparative Example

With the comparative catalyst (type A)) the following parameters were used:
Catalyst mass: 0.5 grams
Volumetric flow rate of feed gas: 100 $cm^3$/min
Molar ratio of methane to oxygen molar in the feed: 4
Kind and volume percent of the inert gas in the feed: He, 60%.

TABLE 1

Data as to selectivity, conversion and yield for the various compounds for the catalyst described in the art. Data are values in %. The selectivity of a particular component is defined as the molar percent of methane converted to that component. Methane conversion is defined as the molar percent of methane converted to other components. Yield of C2 hydrocarbons is the molar percent of feed methane that is converted to C2 hydrocarbons, i.e. is the same as the value of C2 hydrocarbon selectivity, multiplied by the value of methane conversion.

| Temp (° C.) | $S_{C2H4}$ | $S_{C2}$ | $S_{CO2}$ | $S_{CO}$ | $X_{CH4}$ | $Y_{C2}$ |
|---|---|---|---|---|---|---|
| 750 | 0 | 31.46 | 57.87 | 10.67 | 3.75 | 1.18 |
| 800 | 52.07 | 77.54 | 17 | 5.42 | 15.20 | 11.79 |
| 825 | 54.50 | 78.43 | 15.2 | 6.38 | 23.38 | 18.33 |
| 850 | 60.70 | 80.23 | 10.19 | 9.64 | 32.48 | 26.06 |

Example 2

With the catalyst according to the invention the following parameter were used (same as used for the state of the art catalyst):
Catalyst mass: 0.5 grams
Volumetric flow rate of feed gas: 100 $cm^3$/min
Methane to oxygen molar ratio in the feed: 4
Kind and volume percent of the inert gas in the feed: He, 60%.

TABLE 2

Data as to selectivity, conversion and yield for the various compounds for the catalyst according to the invention. Data are values in %.

| Temp (° C.) | $S_{C2H4}$ | $S_{C2}$ | $S_{CO2}$ | $S_{CO}$ | $X_{CH4}$ | $Y_{C2}$ |
|---|---|---|---|---|---|---|
| 750 | 11.35 | 18.91 | 37.91 | 13.10 | 6.17 | 3.02 |
| 800 | 36.08 | 70.42 | 19.34 | 10.25 | 18.82 | 13.25 |
| 825 | 48.17 | 74.69 | 14.6 | 10.35 | 29.55 | 22.08 |
| 850 | 55.84 | 78.03 | 11.39 | 10.58 | 34.91 | 27.24 |

From tables 1 and 2 in the comparative example and Example 2 above it can be seen that according to this invention, despite some loss in C2-hydrocarbon selectivity, a significant improvement in yield of C2 hydrocarbons over the whole temperature range is achieved due to significant increase in methane conversion over the whole temperature range.

The invention claimed is:

1. A catalyst for conversion of methane to a $C_2$ hydrocarbon, said catalyst comprising:
   a) a manganese (Mn) oxide, in combination with an alkali metal and tungsten on a silica support; and
   b) niobium (Nb) as a promoter.

2. The catalyst of claim 1, wherein the catalyst further comprises one or more of Eu (Europium), Y (yttrium) and Nd (neodymium).

3. The catalyst of claim 1, wherein the niobium (Nb) is present in an amount of 0.5 to 5% by weight.

4. The catalyst of claim 3, wherein the niobium (Nb) is present in an amount of 1.2 to 4% by weight.

5. The catalyst of claim 4, wherein the niobium (Nb) is present in an amount of 1.9 by weight.

6. The catalyst of claim 3, wherein the catalyst further comprises one or more of Eu (Europium), Y (yttrium) and Nd (neodymium).

7. The catalyst of claim 1, wherein the niobium is present as niobium oxide.

8. The catalyst of claim 1, wherein the catalyst comprises manganese oxide, tungsten, and sodium as the alkali metal.

9. The catalyst of claim 8, wherein part a) comprises 1.8% manganese oxide, 1.8% sodium oxide and 2.8% tungsten oxide by weight, with the rest silica.

10. The catalyst of claim 1, wherein the catalyst comprises tungsten, an alkali metal, and an additional metal oxide in addition to manganese oxide.

11. The catalyst of claim 1, wherein the alkali metal is sodium.

12. The catalyst of claim 1, wherein the catalyst is prepared by the following process:

a) combining silica with a solution of a soluble manganese salt and a solution of sodium tungstate to obtain a precipitate;
b) drying the precipitate;
c) calcining the precipitate to obtain particles;
d) reducing the size of the particles;
e) combining the particles of step (d) with a solution of a niobium compound to obtain a precipitate; and
f) repeating steps (b), (c) and (d).

13. A process for converting methane to a $C_2$ hydrocarbon comprising the steps of a) contacting a mixture of methane, oxygen and an inert gas with the catalyst of claim 1 to obtain the $C_2$ hydrocarbon; and
b) recovering the $C_2$ hydrocarbon.

14. The process of claim 13, wherein the $C_2$ hydrocarbon recovered is a mixture of ethane and ethylene.

15. The process of claim 13, wherein the process is carried out at a temperature of 600-900° C.

* * * * *